United States Patent
Rizzi et al.

(10) Patent No.: US 10,760,068 B2
(45) Date of Patent: Sep. 1, 2020

(54) HYDROGEL PRECURSOR FORMULATION AND THE USE THEREOF

(71) Applicant: QGEL SA, Lausanne (CH)

(72) Inventors: Simone Rizzi, Ecublens (CH); Jeremy Touati, Sottens (CH)

(73) Assignee: QGEL SA, Lausanne (CH)

(*) Notice: Subject to any disclaimer, the term of this patent is extended or adjusted under 35 U.S.C. 154(b) by 0 days.

(21) Appl. No.: 16/320,164

(22) PCT Filed: Jul. 20, 2017

(86) PCT No.: PCT/EP2017/068381
§ 371 (c)(1),
(2) Date: Jan. 24, 2019

(87) PCT Pub. No.: WO2018/019704
PCT Pub. Date: Feb. 1, 2018

(65) Prior Publication Data
US 2019/0153420 A1 May 23, 2019

(30) Foreign Application Priority Data
Jul. 28, 2016 (EP) ..................... 16181707

(51) Int. Cl.
*C12N 9/74* (2006.01)
*C12N 5/00* (2006.01)

(52) U.S. Cl.
CPC ......... *C12N 9/6429* (2013.01); *C12N 5/0018* (2013.01); *C12N 5/0068* (2013.01); *C12N 2523/00* (2013.01); *C12N 2533/30* (2013.01); *C12N 2533/50* (2013.01); *C12N 2537/10* (2013.01); *C12Y 203/02013* (2013.01); *C12Y 304/21005* (2013.01)

(58) Field of Classification Search
CPC ...... C12N 9/6429; C12N 5/00; C12N 5/0018; C12N 5/0068; C12N 2537/10; C12Y 304/21005; C12Y 203/02013
See application file for complete search history.

(56) References Cited

FOREIGN PATENT DOCUMENTS

| EP | 2 380 920 A1 | 10/2011 |
| WO | 2014/180970 A1 | 11/2014 |
| WO | WO-2014180970 A1 * | 11/2014 |

OTHER PUBLICATIONS

Estroff et al., "Water Gelation by Small Organic Molecules", Chemical Reviews, vol. 104, No. 3, pp. 1201-1218, Feb. 21, 2004, See Spec., p. 1.
Zhang., "Fabrication of Novel Biomaterials Through Molecular Self-Assembly", Nature Biotechnology, Focus on Nanobiotechnology, vol. 21, No. 10, pp. 1171-1178, Oct. 2003, See Spec., p. 1.
Hartgerink et al., "Peptide-Amphiphile Nanofibers: A Versatile Scaffold for the Preparation of Self-Assembly Materials", Proceedings of the National Academy of Sciences, vol. 99, No. 8, pp. 5133-5138, Apr. 16, 2002, See Spec., p. 1.
Sanborn et al., "In Situ Crosslinking of a Biomimetic Peptide-PEG Hydrogel via Thermally Triggered Activation of Factor XIII", Biomaterials, 23, pp. 2703-2710, Dec. 1, 2001, See Spec., p. 2 See European Search See International Search.
Ehrbar et al., "Enzymatic Formation of Modular Cell-Instructive Fibrin Analogs for Tissue Engineering", Biomaterials, 28, pp. 3856-3866, Jan. 23, 2007, See Spec. pp. 21 & 23.
Boll et al., "The Effect of Matrix Characteristics on Fibroblast Proliferation in 3D Gels", Biomaterials, Jun. 16, 2010, See Spec., pp. 22, 23 & 25.
Ranga et al., "Hyaluronic Acid Hydrogels Formed in Situ by Transglutaminase-Catalyzed Reaction", Biomacromolecules, 17, pp. 1553-1560, Nov. 25, 2015, See European Search See International Search.
European Search Report Corresponding to 16181707.7 dated Nov. 11, 2016.
International Search Report Corresponding to PCT/EP2017/068381 dated Oct. 2, 2017.
Written Opinion Corresponding to PCT/EP2017/068381 dated Oct. 2, 2017.

* cited by examiner

*Primary Examiner* — Ruth A Davis
(74) *Attorney, Agent, or Firm* — Davis & Bujold PLLC; Michael J. Bujold

(57) ABSTRACT

A hydrogel precursor formulation which is in the form of an unreacted powder. The formulation comprises an activating enzyme, preferably thrombin, a cross-linking enzyme, preferably a transglutaminase, and more preferably factor XIII transglutaminase. The cross-linking enzyme is activatable by the activating enzyme in water with or without a buffer, and at least one structural compound A. The structural compound is crosslinkable by a selective reaction mediated by the crosslinking enzyme to form a hydrogel, wherein the cross-linking enzyme is activated.

18 Claims, 7 Drawing Sheets

Figure 1A:
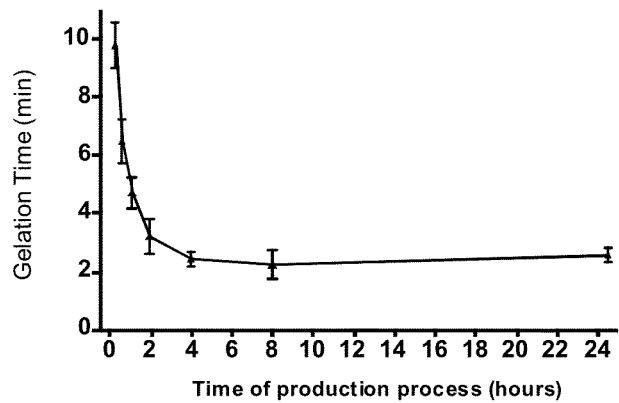

Fig. 6A
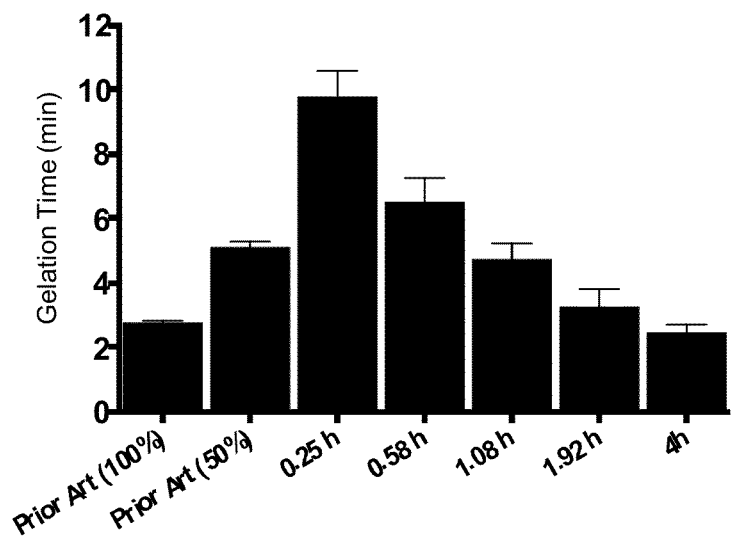
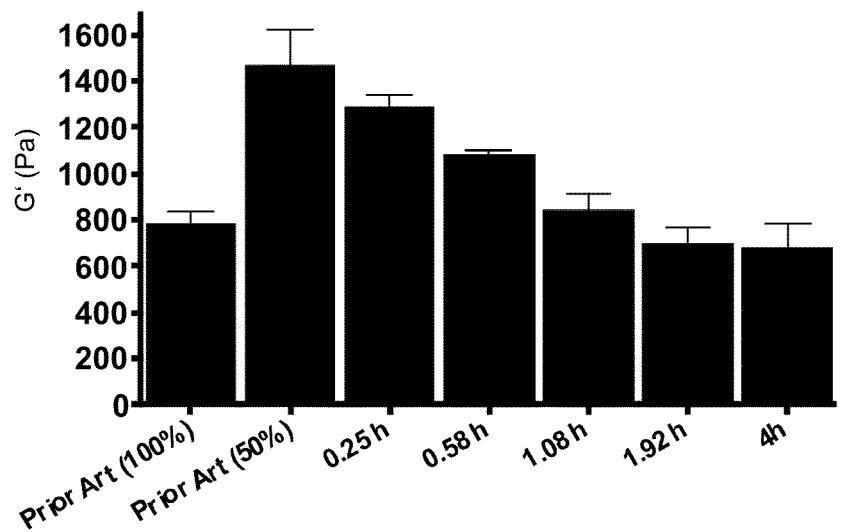
Fig. 6B

HYDROGEL PRECURSOR FORMULATION AND THE USE THEREOF

The present invention relates to hydrogel precursor formulations, a process for the production of a hydrogel precursor formulation, a kit and a method for production of a hydrogel according to the preamble of the independent claims.

Three dimensional cell culture scaffolds have been recognized to allow patterns of gene expression and other cellular activities that more closely mimic living organisms than the conventional two dimensional cell cultures in dishes.

This has led to the development of novel families of synthetic polymer hydrogels, which are often termed artificial ECMs (aECM), since they mimic many aspects of the extracellular matrix. One major challenge is to provide a chemistry which allows cross-linking of the matrix in the presence of cells or biomolecules as well as stable tethering of biomolecules to the matrix itself.

In recent years, different mechanisms were developed allowing the formation of gels in the presence of cells or biomolecules. For example, mechanisms based on the self-assembly of low molecular weight building blocks such as peptides (Estroff et al.: Water gelation by small organic molecules; Chem. Rev. 2004; 104(3); 1201-18) or ureidopyrmimidinone (Zhang S.: Fabrication of novel biomaterials through molecular self-assembly; Nat. Biotechnol. 2003; 21(10); 1171-8) and moderate molecular weight amphiphilic block copolymers (e.g. see Hartgerink et al.: Peptide-amphiphile nonofibers: A versatile scaffold for the preparation of self-assembling materials; Proc. Nat. Acad. Sci. U.S.A. 2002; 99(8); 5133-8) were proposed.

Hydrogels can be produced based on covalent cross-linking of functional groups positioned in hydrogel precursor molecules either by non-enzymatic or enzymatic mechanisms. Enzymatic mechanisms are defined such that the covalent cross-link is mediated by a cross-linking enzyme which catalyzes the cross-linking reaction between functional groups. Cross-linking enzymes known from the blood coagulation system belong e.g. to the class of transglutaminases which catalyse the formation of an isopeptide bond between a amine group such as a protein-/peptide-bound lysine and the acyl group of a protein-/peptide-bound glutamine in the presence of Calcium ions. The use of transglutaminases was adapted to the production of hydrogels in the past.

Hydrogels known in the art are disclosed e.g. in "In situ cross-linking of a biomimetic peptide-PEG hydrogel via thermally triggered activation of factor XIII" by Sanborn et al. (Biomaterials 23 (2002), 2703-2710). Sanborn et al. uses the controlled release of Calcium ion for the activation of hrFactor XIII by thermal triggering of Calcium-loaded liposomes. Upon release of Calcium the gel components are cross-linked by hrFactor XIII. As such the entire gelation system can be stored in an aqueous solution at room temperature without premature gelation.

WO 2014/180970 A1 discloses the production of hydrogels using PEG-based precursor molecules and thrombin-activated factor XIIIa. Factor XIII is reconstituted from lyophilized powder and activated with thrombin for 30 min at 37° C. Aliquots of activated factor XIIIa are stored at −80° C. for further use. Precursor solutions forming hydrogels are prepared in Tris-Buffer (TBS, 50 mM, pH 7.6) containing 50 mM calcium chloride. The cross-linking reaction is initiated by addition of thrombin-activated factor XIIIa and vigorous mixing. One drawback of the process is that a activation of factor XIIIa is separately performed prior to the gel formation step.

It is therefore an objective of the present invention to avoid disadvantages of the known hydrogel precursor formulations, and specifically to provide a hydrogel precursor formulation which reproducibly forms hydrogels. This objective is solved with the hydrogel precursor formulation according to claim 1.

The present invention relates to a hydrogel precursor formulation which is in the form of an unreacted powder. The unreacted powder comprises an activating enzyme, preferably thrombin, and a cross-linking enzyme, preferably a transglutaminase, more preferably factor XIII transglutaminase. The cross-linking enzyme is activatable by the activating enzyme in water with or without a buffer, preferably in water with a conductivity of <5 µS/cm with or without a buffer, and/or preferably having a pH in the range of 5 to 8, more preferably 6 to 8, most preferably 6.5 to 8. Furthermore, the powder comprises at least one structural compound A, preferably two distinct structural compounds A and B. Said structural compound is cross-linkable by a selective reaction mediated by the crosslinking enzyme to form a hydrogel, wherein the cross-linking enzyme is activated preferably with a degree of activation of 50 to 100%, preferred of 75 to 100%, more preferred of substantially 100%. 100% activation means 100% of the factor XIII is activated to factor XIIIa; 75% activation means 75% of the factor XIII is activated to factor XIIIa. 50% activation means 50% of factor XIII is activated factor XIIIa and 50% still factor XIII.

Thus, the hydrogel precursor formulation comprises the essential components required for the production of a hydrogel. This is advantageous as the individual components do not have to be weighed and/or mixed by the end-user. Weighing and mixing is a source of error which is reduced by the formulation according to the invention. The end-user resuspends the hydrogel precursor formulation in an appropriate buffer which provides the conditions, e.g. pH and/or ionic strength, for the formation of a hydrogel. Thus, the reproducibility of the hydrogels produced from the hydrogel precursor formulation is increased and the production of hydrogels is simplified.

Surprisingly, the activated factor XIII is stable in the manufacturing mixture for at least 24 hrs. This means that the resulting physico-chemical properties (e.g. gelation time, Shear modulus G', swelling Q) of hydrogels were unchanged regardless of the duration during which the manufacturing mixture (containing the activated factor XIII) from which the hydrogels originated remained, e.g. at room temperature, before preparation of a hydrogel or lyophilisation (hereinafter "manufacturing time"). Therefore, the stability of the final gel physico-chemical properties of the hydrogels is independent from the manufacturing time of the manufacturing mixture. This illustrates that no loss in activity of the cross-linking enzyme and/or the activating enzyme is observed under these conditions.

The term "room temperature" relates to a temperature in the range of 20 to 25° C. However, an increased temperature, e.g. in laboratories without air condition in tropic countries, may be considered as room temperature.

More preferably the cross-linking enzyme is activatable by the activating enzyme in water with a conductivity of ≤5 µS/cm with or without a buffer and/or <10 ppm Calcium ions and/or <10 ppm Magnesium ions.

The unreacted powder of the hydrogel precursor formulation may comprise particles having any size and shape.

Alternatively, the powder may also be provided as pressed tablet or pill. Most preferably, the powder is provided in the form of a stable compact cake, e.g. at the bottom of a container. This simplifies the handling of the precursor formulation as the powder is positioned at the bottom of a container. Centrifugation prior to dissolving the powder is not necessary in order to concentrate the powder at the bottom. This improves the reproducibility of gel formation.

The powder is unreacted, meaning that almost none of the at least one structural compound A has reacted with a counterpart which participates in the selective reaction forming a cross-link. Preferably more than 70%, more preferably more than 85%, most preferably more than 95% of the compounds have not undergone the selective reaction.

The structural compound A preferably has a functionality of at least three, preferably a functionality of four or more. By "functionality" the number of reactive sites, e.g. reactive groups, on a molecule is meant.

The precursor formulation may be substantially deprived of monovalent ions, wherein the monovalent ion concentration may be preferably in the range of 1 to 60 mM, preferably 10 to 30 mM, if no monovalent ions are added by the end-user. When a hydrogel is produced with a hydrogel precursor formulation deprived of monovalent ions, the amount of monovalent ions in the formed hydrogel is minimized. Thus, the amount of monovalent ions in the formed hydrogel can be adjusted by the buffer added by the end-user depending on the end application. The monovalent ions might have an effect on cells which are embedded in the hydrogel by the end-user. Properties such as cell growth or viability are not negatively influenced by the presence of monovalent ions. Thus, the hydrogel precursor formulation leads to hydrogels which exhibit reduced negative effects on embedded cells.

The precursor formulation may be substantially deprived of divalent ions, preferably Calcium ions, wherein the divalent ion concentration may be preferably <10 µM, more preferably <1 µM, most preferably <10 ppm. The reduction of divalent ions, particularly Calcium ions, present in the hydrogel precursor formulation results in a formulation that does not form a hydrogel prior to the addition of divalent ions. Calcium ions are needed for the catalytic activity of thrombin-activated factor XIII. Therefore, prior to the addition of Calcium ions spontaneous gelation of the precursor formulation including thrombin-activated factor XIII does not occur. Spontaneous gelation is drastically reduced compared to known hydrogel precursor formulations. Thus, gelation of hydrogels is controlled or controllable by using a hydrogel precursor formulation which is substantially deprived of divalent ions, preferably Calcium ions. The amount of calcium ions may be chosen such that no gelation is achieved at room temperature up to 30 hrs, preferably up to 100 hrs, in the presence of 20 U/ml factor XIII, 0.2 U/ml thrombin and 5% w/v structural compound in Tris-Buffer saline (0.65 mM Tris, 1.5 mM NaCl, pH 7.5).

Furthermore, the at least one structural compound A may comprise at least two distinct reactive groups. The distinct reactive groups may be compatible groups, meaning they bond, e.g. cross-link, to each other in order to form a hydrogel through a chemical reaction catalysed by the activated cross-linking enzyme. Alternatively, the precursor formulation comprises a structural compound A and a structural compound B, wherein the structural compound A and the structural compound B differ in size and/or functionality and/or the functional/reactive group. The hydrogel precursor formulation may comprise a structural compound A and a linker compound. "Linker compound" means that the compound forms a linker between two molecules of a structural compound or two molecules of two structural compounds, respectively. The linker compound does not contribute to the 3D nature of the hydrogel, as it is linear/non-branched molecule. "Structural compounds" are defined as branched molecules and therefore they contribute to the 3D structure of hydrogels.

The at least one structural compound A may comprise an acyl moiety, preferably two acyl moieties, more preferably three acyl moieties, and an amine moiety, preferably two amine moieties, preferably three amine moieties. The acyl moiety may be a glutamine and the amine moiety may be a lysine.

If two structural compounds A and B are formulated in the formulation both may comprise at least a glutamine and at least a lysine. Alternatively, one of the two structural compounds A and B comprises at least one glutamine or at least one lysine; the second structural compound comprises the compatible reactive group, either by comprising at least one glutamine or at least one lysine, respectively.

The hydrogel precursor formulation may comprise at least one further hydrogel compound, preferably at least one crosslinkable bioactive compound. The at least one further hydrogel compound, preferably the at least one crosslinkable bioactive compound, may be covalently incorporated in the hydrogel network by cross-linking reactions to two subunits of the hydrogel. The further hydrogel compound may comprise a glutamine and/or lysine. If the further compound only comprises one glutamine or one lysine, the further compound will be incorporated in the gel as a so called dangling molecule, meaning incorporation of the further compounds defines the end of a chain. Here, additional subunits cannot attach.

The bioactive compounds may comprise an RGD peptide sequence e.g. TG-RGDGln peptides such as NQEQVSPL-GRGDSPG-NH2 or TG-RGDLys peptides such as Ac-FKGGRGDSPG-NH2 or the RGD sequence from fibronectin or the YISG sequence from laminin; a growth factor binding site, such as a heparin binding site; a protease binding site or a therapeutically active compound. Preferably, the bioactive compound comprises a cell adhesion site, most preferably an RGD sequence.

The bioactive compound comprises at least one active group capable of undergoing a selective reaction. Preferably, the bioactive compound comprises at least one lysine and/or one glutamine.

The bioactive compound may be conjugatable with the structural compound through a selective reaction. Preferably, this selective reaction is the same reaction as the selective reaction used for the formation of the hydrogel. Alternatively, the bioactive compound may be conjugated to the structural compound through a selective reaction prior to the formation of a hydrogel.

The structural compound may be a multi-branched polyethylene glycol, preferably an 8-arm polyethylene glycol. Preferably, the 8-arm polyethylene glycol has a size in the range of 30 to 50 kDa, preferably 35 to 45 kDa, more preferably of 40 kDa. Each branch of the structural compound preferably comprises a functional group.

A further aspect of the invention relates to a process for the production of a hydrogel precursor formulation in the form of an unreacted powder. The process for the production comprises the steps a), b) and optionally c).

Step a) includes mixing of an activating enzyme, a cross-linking enzyme and at least one structural compound A in water with or without a buffer, preferably in water with a conductivity of <5 µS/cm with or without a buffer and/or preferably having a pH in the range of 5 to 8, more preferably 6 to 8, most preferably 6.5 to 8. The cross-linking enzyme is activatable by the activating enzyme in said water.

The activating enzyme is preferably thrombin. The cross-linking enzyme is preferably a transglutaminase, more preferably factor XIII transglutaminase. Preferably two distinct structural compounds A and B are mixed in step a).

Step b) may be carried out before or after step a). It includes incubation of the cross-linking enzyme and the activating enzyme for a time sufficient that the gel characteristics, such as gelation time, shear modulus G' and swelling Q, of a gel produced from the hydrogel precursor formulation remain substantially constant independent from the duration of the manufacturing time. Substantially constant means that the change of the gel characteristics over time is smaller than 15%, preferably smaller than 10%, more preferably smaller than 5%. Experiments have shown that with a sufficient incubation a plateau of the aforementioned characteristics is reached (see below), this means that the characteristics do not change, irrespective of the manufacturing time. Option i) relates hereinafter to step b) is carried out after step a). Option ii) relates hereinafter to step b) is carried out before step a).

Preferably, the cross-linking enzyme and the activating enzyme is incubated for a time sufficient and under conditions such that a hydrogel producible or produced with the precursor formulation has a gelation time preferably in the range of 0.5 to 30 min, more preferably 1 to 20 min, most preferably 2 to 10 min, when 1 to 20% w/v structural compound, 0.1 to 100 U/ml cross-linking enzyme and 0.001 to 20 U/ml activating enzyme are used in a buffer comprising calcium ions in the range of 1 to 200 mM, preferably 10 to 100 mM, with a pH in the range of 6.5 to 8.5 at a temperature of 4 to 37° C.

Preferably, the cross-linking enzyme and the activating enzyme is incubated for a time sufficient and under conditions such that a hydrogel producible or produced with the precursor formulation has a shear modulus G' preferably in the range of 100 to 15'000 Pa, more preferably 200 to 5'000 Pa when 1 to 20% w/v structural compound, 0.1 to 100 U/ml cross-linking enzyme and 0.001 to 20 U/ml activating enzyme are used in a buffer comprising calcium ions in the range of 1 to 200 mM, preferably 10 to 100 mM, with a pH in the range of 6.5 to 8.5 at a temperature of 4 to 37° C.

Preferably, the cross-linking enzyme and the activating enzyme is incubated for a time sufficient and under conditions such that a hydrogel producible or produced with the precursor formulation has a swelling ratio Q preferably in the range of 10 to 100, more preferably 20 to 80, when 1 to 20% w/v structural compound, 0.1 to 100 U/ml cross-linking enzyme and 0.001 to 20 U/ml activating enzyme are used in a buffer comprising calcium ions in the range of 1 to 200 mM, preferably 10 to 100 mM, with a pH in the range of 6.5 to 8.5 at a temperature of 4 to 37° C.

Optional Step c) includes after the later of steps a) or b) lyophilisation of the mixture.

The structural compound is crosslinkable by a selective reaction mediated by the crosslinking enzyme. The components are mixed in step a) under conditions, which hinder the cross-linking reaction mediated by the cross-linking enzyme.

The process for the production of a hydrogel precursor formulation according to the invention is advantageous as either i) all components, such as cross-linking enzyme, activating enzyme and structural compound(s) are mixed and prepared as a ready-to-use powder (step b) after a) according to option i)) or ii) the cross-linking enzyme is activated in water, preferably with minimal conductivity as indicated, with or without a buffer prior to the mixing with the remaining gel compound(s) (step b) before a) according to option ii)).

Option i) simplifies the production process of hydrogel precursor formulations as mixing of gel components is performed in only one step. The formation of hydrogels is also simplified as the ready-to-use powder is resuspended in a buffer and addition of the cross-linking enzyme to hydrogel precursors is not required. Over all, reproducibility of the aforementioned processes is improved. In option i), the incubation time is equal the manufacturing time.

Option ii) allows adaptation of the hydrogel system to the needs of the end-user as the final concentration of the cross-linking enzyme for the formation of the hydrogel may be freely selectable. Here, the final concentration of the cross-linking enzyme is independent from the dry mass of the hydrogel precursors as the activated cross-linking enzyme may be added to the hydrogel compounds prior to the formation of the hydrogel. In option ii) the hydrogel precursors and the activated cross-linking enzyme may be lyophilized either premixed or in separate containers.

By way of example, according to option ii), the cross-linking enzyme factor XIII is activated by the activating enzyme thrombin in water with a conductivity of <5 µS/cm with a pH in the range of 6 to 8 or in Tris-Buffer saline (e.g. 0.9 mM Tris, 13 mM NaCl, pH 7.6) in the absence of Calcium ions at 37° C. for 30 min. Interestingly, the activated factor XIII is stable when mixed in the manufacturing mixture for up to 24 hrs at room temperature. This means that the resulting physico-chemical properties (gelation time, shear modulus G', swelling Q) of hydrogels were unchanged regardless of the duration during which the manufacturing mixture (containing the activated factor XIII and hydrogel precursors) from which the hydrogels originated remained at room temperature before lyophilisation. Therefore, the stability of the final gel physico-chemical properties is independent from the manufacturing time. This illustrates that no loss in activity of the cross-linking enzyme and/or the activating enzyme is observed under these conditions.

The incubation of the mixture obtained in step a) may be performed for at least 0.5 h, preferably less than 24 hrs, more preferably 2 to 4 hrs, at a temperature in the range of 4 to 37° C., preferably 10 to 25° C., more preferably at room temperature.

If step b) is performed before step a) according to option ii) incubation of the mixture in step b) is preferably performed for 15 min to 1 hr, particularly 30 min, at 37° C. If step b) is performed after step a) according to option i) incubation of the mixture in step b) is preferably performed for 2 to 4 hrs at 20° C. or for 1 to 2 hrs at 37° C. in order to reach a plateau wherein the gel properties (gelation time, shear modulus G', swelling Q) of a hydrogel produced from the hydrogel precursor formulation are substantially constant. In option i), the incubation time is basically equal to the manufacturing time.

The cross-linking enzyme may have a degree of activation of 50 to 100%, preferably of 75 to 100%, more preferably of substantially 100%, after step b).

Furthermore, at least one further hydrogel compound, preferably at least one cross-linkable bioactive compound, may be added in step a). The at least one further hydrogel compound, preferably the at least one cross-linkable bioactive compound, may be covalently incorporated in the hydrogel network by selective cross-linking reactions to at least one subunit of the hydrogel. The further hydrogel compound may comprise a glutamine and/or lysine. If the further compound only comprises one glutamine or one lysine, the further compound will be incorporated in the gel as a so called dangling molecule, meaning incorporation of the further compounds defines the end of a chain of conjugated subunits. Here, additional subunits cannot attach.

The process for the production of a hydrogel precursor formulation may use a mixture in step a) comprising 1 to 100 U/ml, preferably 2 to 50 U/ml, more preferably 4 to 25 U/ml, of the cross-linking enzyme and/or 0.01 to 10 U/ml, preferably 0.02 to 5 U/ml, more preferably 0.04 to 0.7 U/ml of the activating enzyme.

The process may use a mixture in step a) comprising 0.5 to 25% w/v, preferably 1 to 20% w/v, more preferably 2 to 10% w/v, of the at least one structural compound A.

The process may use a mixture in step a) comprising 0.005 to 10% w/v, preferably 0.01 to 2% w/v, of a cross-linkable bioactive compound such as a peptide. Alternatively, the mixture in step a) may comprise 0.005 to 5 mg/ml, preferably 0.2 to 2.5 mg/ml, of a cross-linkable bioactive compound such as a recombinant protein or a protein purified from human or animal tissue. An exemplary protein is laminin.

The buffer compositions used in the process for production of the hydrogel precursor formulation according to the invention may comprise measures to minimize the concentration of free divalent ions, particularly free Calcium ions. These measures are for example chelating agents such as EDTA or EGTA. Depending on the cell type and the time of exposure, EDTA concentrations in the range of 100 to 500 µM may be toxic for the cells. However, when the cells are encapsulated in the hydrogels and placed in a medium, the EDTA concentrations is diluted by a factor of 3 to 10. The EDTA may be removed by change of the medium, e.g. washed out.

Furthermore, the mixture comprising hydrogel precursors in the process for the production of a hydrogel according to the invention may comprise filtration, preferably sterile filtration, of the mixture prior to lyophilisation. This results in a precursor formulation, which is deprived of contaminating and possibly harmful components, e.g. bacteria.

The mixture obtained in step a) may be sterile filtrated and/or aliquoted in order to handle volumes which are useful for downstream processing.

After lyophilisation the Oxygen content of the precursor formulation may be reduced by storage of the formulation in an inert gas atmosphere such as nitrogen. This minimizes oxidative processes induced by oxygen in the precursor formulation and hence increases the storability of the formulation.

A further aspect of the invention relates to a hydrogel precursor formulation obtainable or obtained by the process according to the invention as discussed.

A further aspect of the invention relates to a kit which comprises at least one container filled with a hydrogel precursor formulation as discussed, a container with a reaction buffer and optionally user instructions. The kit provides all essential components for the production of a hydrogel to facilitate fast and straight-forward production of hydrogels by an end-user.

The reaction buffer of the kit may contain Calcium ions in the range from 1 to 200 mM, preferably 10 to 100 mM, more preferably 20 to 100 mM. The calcium ions which are essential for the activity of the cross-linking enzyme, preferably the transglutaminase, more preferably the factor XIII transglutaminase, are provided by the reaction buffer and thus formation of the hydrogel is triggered by resuspending the powder of the hydrogel precursor formulation in the reaction buffer. The reaction buffer is preferably a saline buffer solution, more preferably a Tris-buffer saline solution (TBS).

Furthermore, the reaction buffer may have a pH in the range of 5 to 8, preferably 6 to 8, more preferably 6.5 to 8.

A further aspect of the invention relates to a method of production of a hydrogel comprising the steps of resuspending a hydrogel precursor formulations as discussed in a reaction buffer, preferably comprising Calcium ions, and optionally adding a cell culture suspension.

At least one gel may be casted with the hydrogel precursor solution in the method of production of a hydrogel.

The gelation time of the gel precursor solution may be in the range of 1 to 20 min, preferably 2 to 10 min, more preferably 2 to 7 min, at a temperature in the range of 4 to 37° C., preferably 10 to 30° C., more preferably 15 to 25° C. The gelation time is the time in which the gel precursor solution is liquid before gelation occurs.

The polymerization time of the gel precursor solution may be in the range of 10 to 60 min, preferably 15 to 45 min, at a temperature in the range of 4 to 37° C., preferably 37° C. The polymerization time is the time starting with the end of the gelation time and continues until completion of the gel polymerization.

Polymerization of the gel precursor solution is preferably performed at 37° C. and/or in a humidified atmosphere for cell culture.

A cell culture medium or a buffer may be added after polymerization.

Compounds

The structural compounds are preferably selected from the group consisting of oligomers, polymers, biosynthetic or natural proteins or peptides and polysaccharides. Preferably, the structural compounds are polymers selected from the group consisting of poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly(propylene oxide) block copolymers or mixtures thereof. The structural compounds are more preferably branched poly(ethylene glycol) with three, four or more arms, most preferably eight-arm poly(ethylene glycol).

Figure 1B:
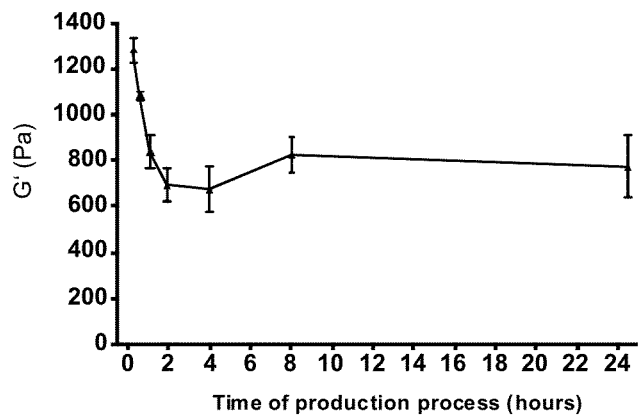
Figure 1C:
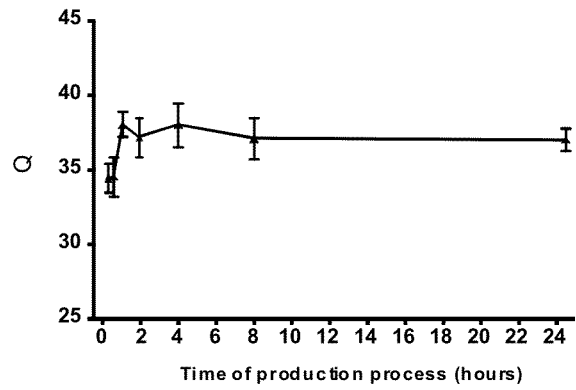
Figure 2A:
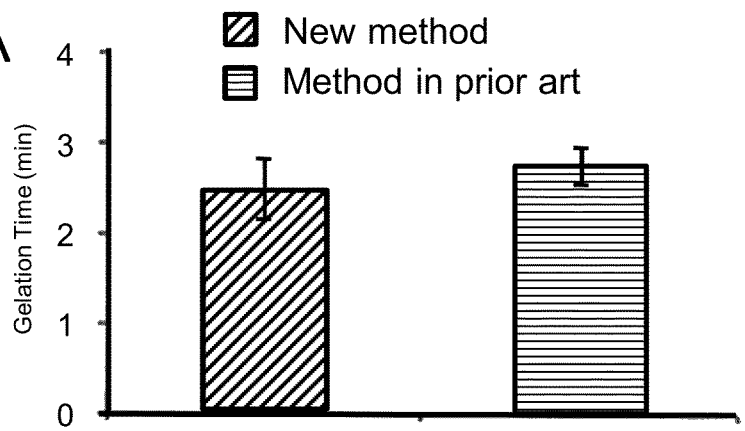
Figure 2B:
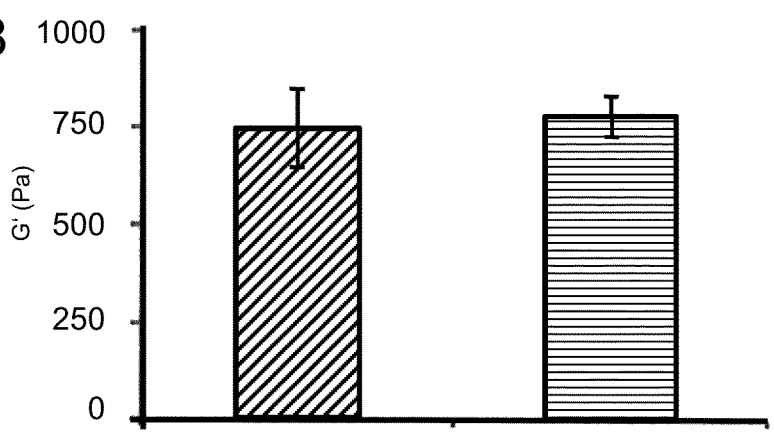
Figure 2C:
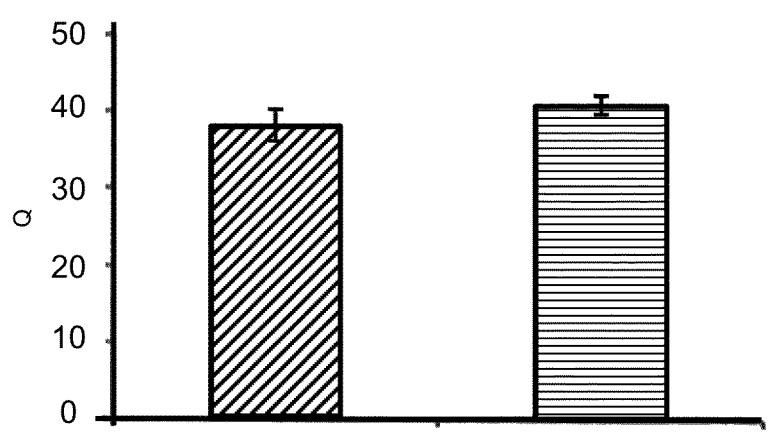
Figure 3A:
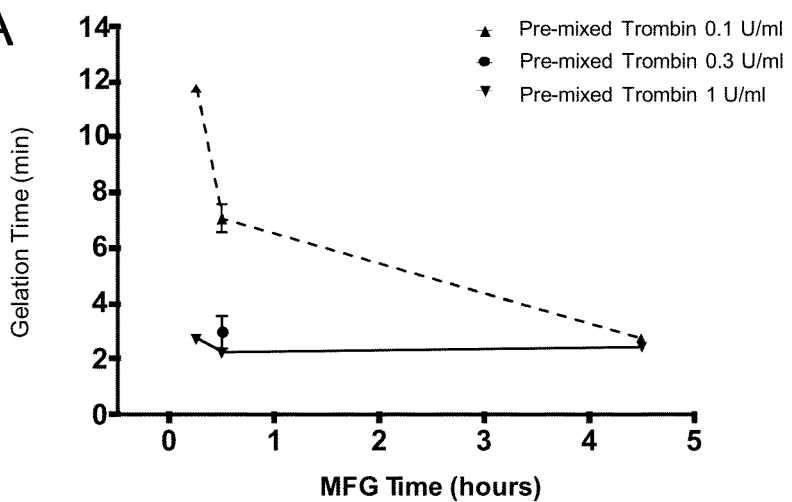
Figure 3B:
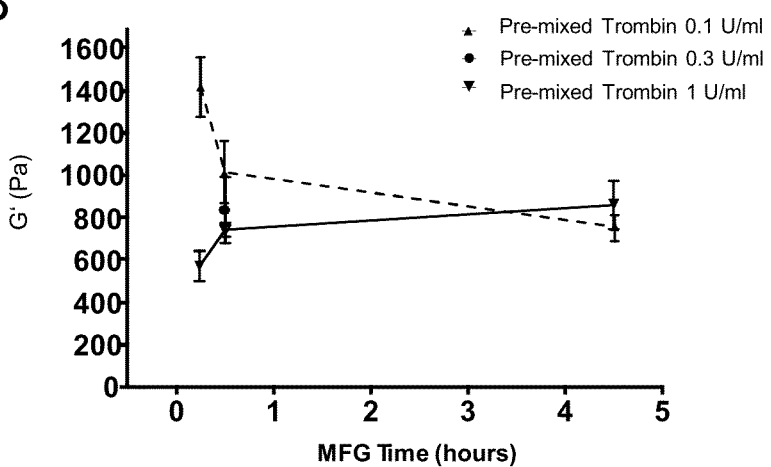
Figure 3C:
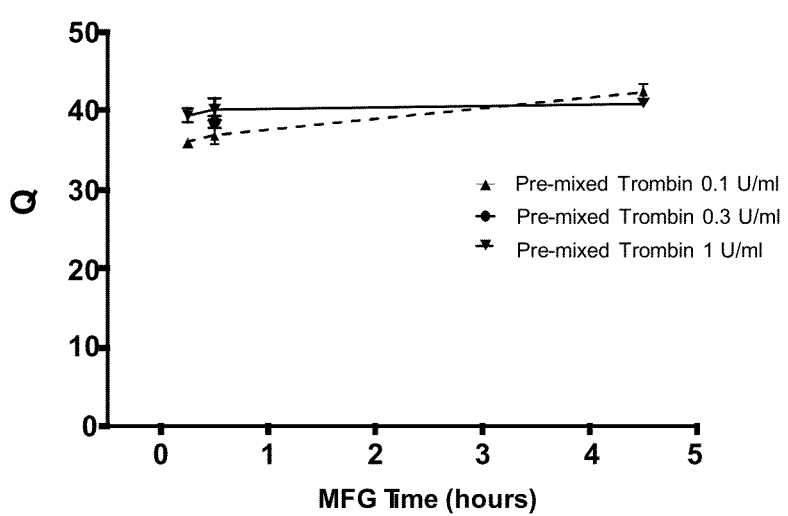
Figure 5A:
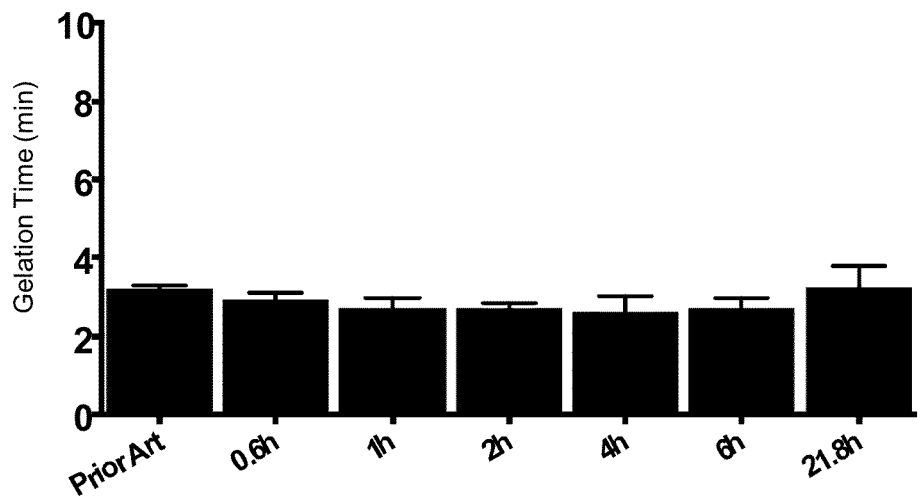
Figure 5B:
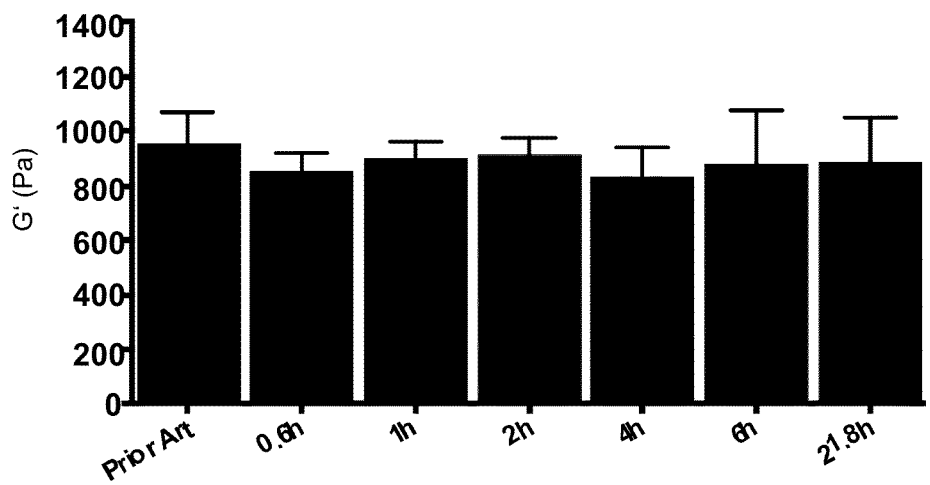
Figure 5C:
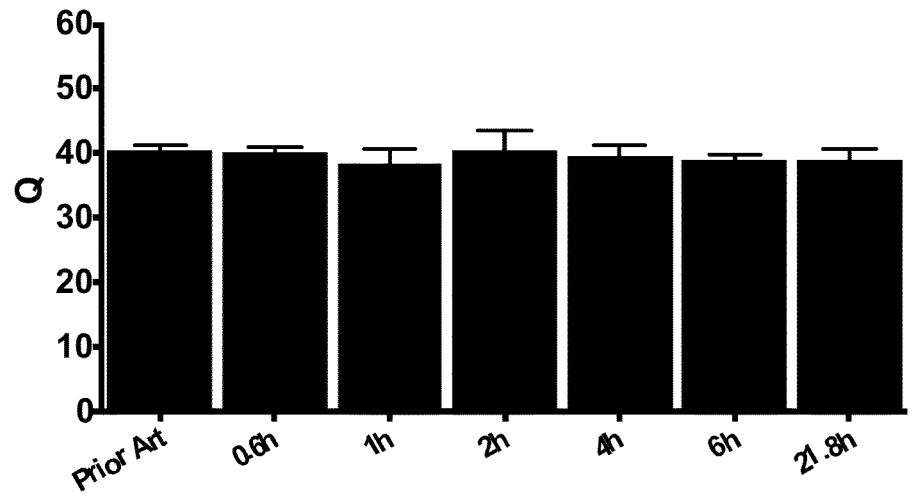
Figure 7:
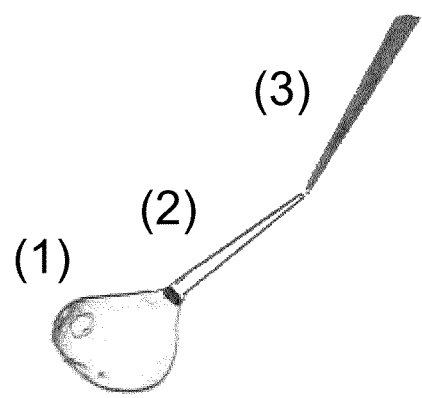

Further aspects and details of the present invention will become apparent from the figures and examples given in the following, which show:

FIG. 1: Properties of hydrogels as a function of time (production time) during which the manufacturing mixture comprising gel precursors in solution, factor XIII and thrombin was processed before freezing and lyophilisation; the powder was subsequently resuspended to form hydrogels and measurement of their properties;

FIG. 2: Properties of hydrogels produced from hydrogel precursor formulations according to the invention compared to a hydrogel described in WO 2014/180970 A1;

FIG. 3: Properties of hydrogels depending from production time of manufacturing mixtures comprising gel precursors in solution, factor XIII and thrombin with different concentrations before freezing and lyophilisation; the powder was subsequently resuspended to form hydrogel and measurement of their properties;

FIG. 4: Hydrogel precursors for the use in single component gels (C; D) and two component gels (A; B);

FIG. 5: Properties of hydrogels produced from hydrogel precursor formulations according to the invention over increasing manufacturing times compared to a hydrogel described in WO 2014/180970 A1;

FIG. 6: Activation range of factor XIII in the manufacturing mixture over time according to the invention;

FIG. 7: Photograph of the end point of the gelation time of a liquid gel drop.

FIG. 1 shows plots of properties of hydrogels as a function of time (manufacturing time, which is the "time of production process") during which the mixture including gel precursors in solution, factor XIII and thrombin was kept at room temperature prior to freezing and lyophilisation.

The hydrogels according to the invention were produced as outlined for FIG. 6 (step a), then step b) and step c) according to option i)). These properties relate to gelation time (A), Shear modulus G' (B) and swelling Q (C). A mixture comprising 5% w/v of a structural compound A (functionalized with a Glutamine-containing substrate) and B (functionalized with a Lysine-containing substrate), factor XIII at 20 U/ml and thrombin at 0.2 U/ml without Calcium ions was prepared and left and room temperature (20 to 25° C.). At various time points the mixture was used to fill vials that were frozen at −80° C. and subsequently lyophilised. After the lyophilisation the vials were sealed, capped and stored at −20° C. Thereafter, the vials were used to form gels with structural compounds at 2.5% w/v by resuspending the lyophilized mixture in an appropriate buffer (Tris-Buffer, 50 mM; pH 7.6) containing 50 mM Calcium ions to induce gelation catalysed by the activated factor XIII at a final concentration of 10 U/ml. The plots A, B and C of FIG. 1 show that a horizontal plateau of final hydrogel properties is reached approximately after 2 to 4 hrs of the manufacturing time. This means, that a production process of more than 2 hrs has no effect on the final hydrogel properties. The hydrogel characteristics (hydrogel properties) remain substantially constant when the manufacturing time exceeds 2 hrs.

FIG. 2 shows a comparison of properties of hydrogels produced according to the process of the present invention according to option i) (left bar in A, B and C) and according to the prior art method of WO 2014/180970 A1 (right bar in A, B and C). The mixture according to the invention was prepared as described for FIG. 1, wherein manufacturing times result in a horizontal plateau of final hydrogel properties (here the hydrogel properties remain substantially constant). WO 2014/180970 A1 discloses a separate activation of factor XIII by thrombin in a Calcium containing buffer at 37° C. for 30 min prior to freezing of the activated factor XIII, which is added thereafter to hydrogel precursor solutions for the hydrogel formation. The comparison of the data illustrates that the hydrogels produced according to the process of the present invention without separate preactivation of factor XIII surprisingly exhibit similar gelation time, Shear modulus G' and swelling Q as hydrogels known in the art. However, products resulting from the process of the invention are easier to handle for the end-user, since the lyophilized powder can be used directly by addition of an appropriate buffer to engage the cross-linking reaction without weighing and less mixing steps, which may cause errors.

FIG. 3 shows a comparison of properties of hydrogels depending from manufacturing time wherein the mixture comprising the gel precursors in solution, factor XIII and thrombin with different concentrations was kept at room temperature prior to freezing and lyophilisation. Thrombin was present in the mixture reaching final concentrations in resulting gels of 0.1 U/ml, 0.3 U/ml and 1 U/ml. The graphs A, B and C illustrate that the horizontal plateau representing final gel properties (gelation time, shear modulus G', swelling Q) is reached faster by using higher concentrations of thrombin in the mixture. The mixture was prepared as indicated for FIG. 1 (according to option i)) with manufacturing times for each thrombin concentrations indicated in the horizontal axis (X-axis) of the graphs.

FIG. 4 shows gel components which may be used in the hydrogel precursor formulation or the process for production of a hydrogel precursor formulation according to the invention. Structural compounds of single component gels (C, D) and two component gels (A, B) are shown. Functional molecules such as Gln-containing substrate for factor XIII crosslinking referred to as X and Lys-containing substrate for factor XIII cross-linking referred to as Y are coupled to poly(ethylene glycol) arms. FIG. 4C shows a 4-arm poly (ethylene glycol) as structural component comprising two Glutamine and two Lysine residues. FIG. 4D shows an 8-arm poly(ethylene glycol) as structural component comprising four Glutamine and four Lysine residues. As such, the structural components of FIGS. 4C and 4D form a polymeric network, e.g. a hydrogel upon cross-linking catalysed by factor XIII in the presence of Calcium ions.

Figure 4A:
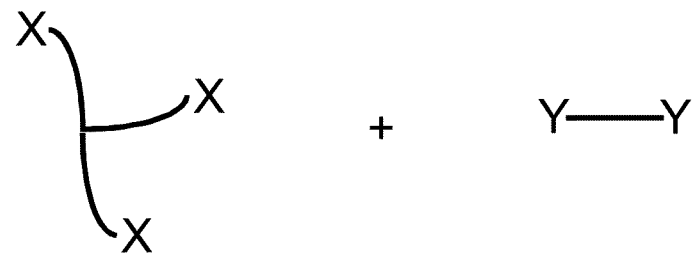

Two component gels require two distinct types of molecules wherein e.g. the structural component is a multi-arm poly(ethylene glycol) comprising at least three Glutamine residues and a linker compound comprises two Lysine residues (FIG. 4A). The linker compound covalently couples individual molecules of the structural compound upon cross-linking catalysed by factor XIII in the presence of Calcium ions. However, the linker compound does not contribute directly to the 3D nature of the hydrogel which is facilitated by the branched structural compound.

Figure 4B:
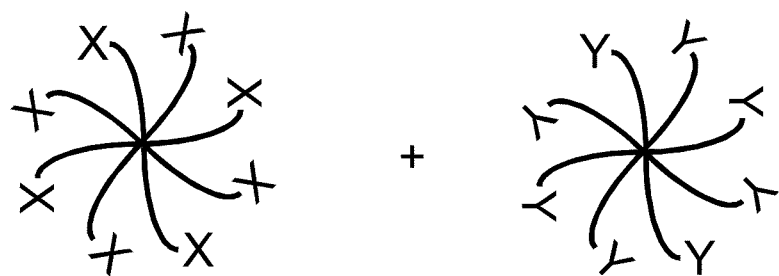
Figure 4C:
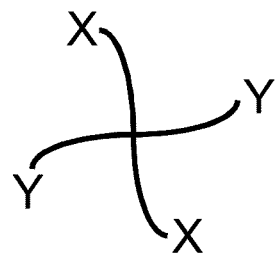
Figure 4D:
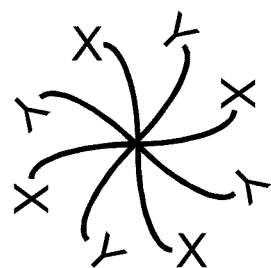

In FIG. 4B a scenario of two structural compounds A and B is shown. The structural compounds A and B base on an 8-arm poly(ethylene glycole) functionalized with a Gluta-mine-containing substrate (structural compound A) and a Lysine-containing substrate (structural compound B). Both structural compounds contribute to the 3D nature of the formed hydrogel upon cross-linking catalyzed by factor XIII in the presence of Calcium ions.

FIG. 5

FIG. 5 shows properties (namely gelation time, shear modulus G', swelling Q) of hydrogels produced from hydrogel precursor formulations according to the invention, namely option ii) (step b) before step a) followed by step c), over increasing manufacturing times compared to a hydrogel as described in WO 2014/180970 A1.

The hydrogels produced from hydrogel precursor formulations according to the invention were produced as follows:

Functionalization of multiarm-PEG (8arm-PEG-OH, $M_n$=40 kDa, Nektar, Huntsville, Ala., USA) with vinyl sulfone groups (8arm-PEG-VS) were performed as previously described (Ehrbar M, Rizzi S C, Hlushchuk R, Djonov V, Zisch A H, et al. (2007) Enzymatic formation of modular cell-instructive fibrin analogs for tissue engineering. Biomaterials 28: 3856-3866.; Bott K, Upton Z, Schrobback K, Ehrbar M, Hubbell J A, Lutolf M P, Rizzi S C, The effect of matrix characteristics on fibroblast proliferation in 3D gels, Biomaterials. 2010 Nov.; 31(32):8454-64). Briefly, peptides (Bachem. Switzerland) containing complementary substrates for FXIII-catalysed cross-linking, NQEQVS-PLERCG-NH2 (TG-Gln) or Ac-FKGGGPQGIWGQERCG-NH 2 (W-Lys) were coupled to 8arm-PEG-VS via Michael-type conjugate addition between vinyl sulfone groups of end-functionalized PEG and thiols of peptide cysteine residues, yielding the hydrogel precursors TG-PEG 8-arm (Structural compound A) and Lys-PEG 8-arm (Structural compound B), respectively. After the coupling reaction the solutions were dialysed extensively against ultra pure ddH2O and were subsequently freeze-dried. The W-Lys peptide also included a matrix metalloproteinase (MMP) substrate to render the final hydrogels susceptible to proteolytic degradation. It is also possible to make gels with other types of kinetics and/or sensitivities to other proteinases by modifying the amino acid sequence accordingly.

Hydrogels tested for FIG. 5 were produced according to the method of the invention including the Steps: Step a), Step b) before Step a), and Step c) according to option ii).

Compounds used were prepared as described above. Briefly, FXIII (172 or 200 U/mL final) and thrombin (1.72 or 2 U/mL final) in water or buffer (1 mM Tris-Buffer with 15 mM NaCl, in the absence of Ca2+) were mixed and pre-incubated at 37 C for 30 min (step b). Factor XIII is thus fully activated before used in step a). Subsequently, this FXIII/thrombin solution was mixed at room temperature with a solution containing both Structural compounds A and B in water (conductivity of <5 µS/cm) with stoichiometrically balanced reacting groups (step a). When required a crosslinkable bioactive compound, e.g. TG-RGDGln can also be added to the manufacturing mixture. When required a cross-linkable bioactive compound, e.g. TG-RGDGln can also be added to the manufacturing mixture. After step a) at specific time points (as indicated in the x-axis of the charts) samples were aliquoted, frozen and step c) performed. After re-suspension of the unreacted powder-pre-mixes (that include an activating enzyme, thrombin, a cross-linking enzyme, FXIII, and Structural compounds A and B, and optionally a bioactive compound TG-RGDGln) with an appropriate buffer (see below), the resulting gels have the same final composition and characteristics as the one described for the prior art below.

Prior art method—FXIII-catalysed PEG-based hydrogels (Gels) formed using prior art methods and used as benchmark for hydrogels produced with the now process described in this application In order to pre-activate factor XIII (FXIII) to FXIIIa, FXIII (Behring, Switzerland) was activated as described in prior art to form FXIIIa (Ehrbar M, Rizzi S C, Hlushchuk R, Djonov V, Zisch A H, et al. (2007) Enzymatic formation of modular cell-instructive fibrin analogs for tissue engineering. Biomaterials 28: 3856-3866.; WO 2014/180970 A1; Bott K, Upton Z, Schrobback K, Ehrbar M, Hubbell J A, Lutolf M P, Rizzi S C, The effect of matrix characteristics on fibroblast proliferation in 3D gels, Biomaterials. 2010 Nov.; 31(32):8454-64.). Briefly, reconstituted FXIII from lyophilized powder (172.41 or 200 U/mL) was activated with human thrombin (Sigma, 1.72 or 2 U/mL) for 30 min at 37° C. in 1 mM Tris-Buffer with 15 mM NaCL and 2.5 mM $CaCl_2$ (pH 7.6). Subsequently, aliquots of FXIIIa are stored at −80° C. and used to form gels as described below.

Briefly, gels were formed by FXIII-catalysed cross-linking of stoichiometrically balanced TG-PEG 8-arm (Structural component A) and Lys-PEG 8-arm (Structural component B), produced as described above. For example, 100 uL of gel (2.5% w/v dry mass) contains 1.22 mg of Structural component A and 1.28 mg Structural compound B. The gel formation reaction normally occurs in Tris-Buffer (TBS, 50 mM, pH 7.6) containing 50 mM calcium chloride and a final concentration of FXIIIa of 10 U/mL, which is added as last step after mixing Structural compounds A and B. When required a crosslinkable bioactive compound exemplified with the cell adhesion peptide RGD (TG-RGDGln, amino acid sequence: NQEQVSPL-GRGDSPG-NH2; Bachem, Switzerland) is also added in the gel formation reaction (50 µM final concentration in gel) before addition of FXIIIa. The cross-linking reaction mixture is then incubated at 37° C. and in a 5% CO2 humidified atmosphere for 30 to 45 min.

Hydrogel Mechanical and Swelling Tests

Gelation time is the time that the gel precursor solution handled by the end-user to make gels remains liquid before becoming solid and start being a gel that can no longer be handled with liquid handling devices. Briefly, when the unreacted powder pre-mixes (produced as described in this invention and containing all compounds to make gels) are re-suspended by the end-user with an appropriate buffer, cross-linking reaction (i.e. gelation) starts, and time is measured until the liquid solution 1 forms a "little filament" 2 sticking to the pipette tip 3 as illustrated in FIG. 7. The filament 2 is an indication that this hardening gel solution 1 can no longer be handled by end users with liquid handling devices. Polymerization reaction to form the final gel is then continuing until the reacting groups are consumed. The same measurements are performed for gels prepared with the prior art method, and in this case gelation time measurements start when the pre-activated FXIII (FXIIIa) is added by the end user as last ingredient to the solution containing all gel compounds to start cross-linking reaction.

Gels (e.g. 2.5% w/v dry-mass) were prepared as described above in the different manufacturing protocols. Liquid drops of gels before hardening (80 µL volume) were sandwiched between sterile hydrophobic glass microscopy slides (coated with SigmaCote, Sigma, USA) with 1 mm thick spacers and were gelled at 37° C. and 5% CO2 humidified atmosphere for 45 min. After completion gelation and swelling in PBS for 24 h, gel discs of 8 mm in diameter were produced using a biopsy punch and were then stored in the same buffer prior to mechanical measurements.

Rheological measurements were performed using an (MCR 302, Anton Paar). Gels were placed between the two parallel plates of the rheometer and compressed up to 80% of their original thickness to avoid slipping. Strain sweeps at constant frequencies were conducted in order to confirm that measurements were performed within the linear viscoelastic behaviour range of the hydrogels. Elastic shear modulus (G') were recorded at constant strains as a function of the frequency. The value of G' for each swollen disc sample was calculated as the average of the G' values measured between 0.1 and 0.2 Hz. All measurements were conducted at room temperature (22° C.). Swelling Q ($=w_s/w_d$) was calculated as the weight ratio of hydrogels at swelling equilibrium in PBS ($w_s$) and their theoretical dry-mass ($w_d$) (Bott K, Upton Z, Schrobback K, Ehrbar M, Hubbell J A, Lutolf M P, Rizzi S C, The effect of matrix characteristics on fibroblast proliferation in 3D gels, Biomaterials. 2010 Nov.; 31(32):8454-64.).

FIG. 5 shows the results obtained using the method according to the invention (option ii) compared with the prior art methods as described above.

The method according to option ii) corresponds to the manufacturing process including the following steps: Step b) then Step a) and Step c). Briefly, the cross-linking and activating enzymes were premixed and pre-incubated for 30 min at 37 C (Step b)). Subsequently, the structural compounds were added to the enzyme premix at room temperature (manufacturing mixture starts) (Step a)) and sterile filtered, then at 0.6 h, 1 h, 2 h, 4 h, 6 h and 21.8 h aliquots of the manufacturing mixture are lyophilized (Step c)).

The pre-incubation of FXIII with thrombin in the absence of Ca2+ was performed at 37° C. for 30 min before mixing with the rest of the precursor solution (including the structural compounds) to generate the manufacturing mixture. This way of pre-incubation is beneficial, as FXIII seems to be already activated to 100% (and/or similar as to the prior art). Subsequently, regardless of the duration the manufacturing mixture was left at room temperature (manufacturing time) before lyophilisation, final gel properties did not change. The graphs A, B and C in FIG. 5 illustrate that the final gel properties (gelation time, shear modulus G', swelling Q) are stable over the manufacturing time, i.e. the time the manufacturing mixture remained at room temperature before lyophilisation. Furthermore, the final gel properties are similar to those obtained with the prior art method.

FIG. 6

FIG. 6 shows the activation of factor XIII in the manufacturing mixture over time according to the invention (option i).

Hydrogels produced according to the method of the invention including the steps: Step a), Step b) after step a), and Step c) according to option i).

In the following, it is exemplified how unreacted powder-pre-mixes are produced that include an activating enzyme (thrombin), a cross-linking enzyme (FXIII), Structural compounds A and B, and optionally a bioactive compound TG-RGDGln. These lyophilized pre-mixes are then use by an end-user to form 2.5% w/v dry-mass gels. The final 2.5% w/v gels contain the exact same Structural (and bioactive) compounds, concentrations of FXIII and thrombin as the 2.5% w/v gels produced with the prior art method outlined for FIG. 5.

5% w/v solutions of both structural compounds A and B (produced as outlined above) were made in water with a conductivity of <5 µS/cm), and mixed with stoichiometrically balanced reacting groups. FXIII and thrombin (both dissolved in water in separate containers) were mixed with the 5% w/v Structural compound mixture to reach a final concentration of approx. 20 U/mL and 0.2 U/mL, respectively. The ratio Units FXIII to Units thrombin was kept at 100 to 1 to mimic the ratio of cross-linking enzyme and activation enzyme as in the prior art condition.

When required a cross-linkable bioactive compound, e.g. TG-RGDGln can also be added to the manufacturing mixture. The preparation of the manufacturing mixture was performed in the absence of Ca2+ and the process was performed at room temperature. The pH of the manufacturing mixture ranges from 6.5-8.

After mixing all compounds as indicated above, the manufacturing mixture was then sterile filtered using e.g. conventional syringe filters with 0.22 µm pore sizes. Subsequently, the sterile solution was filled into containers that are made for lyophilisation to obtain the unreacted powder ready to use.

Generally speaking, at specific time points (between 0.25 and 25 hours of incubation of the manufacturing mixture at room temperature; cp. FIGS. 1 and 6) aliquots were frozen and lyophilized to generate the unreacted powder (at the bottom of the container) with all compounds required to make gels. The gel properties (gelation time, shear modulus G') of gels produced from such manufacturing mixtures that stayed at room temperature for more than 2 to 4 h remained stable (see below).

Preparation of Gels by Re-Suspension of the Lyophilized Unreacted Powder Containing all Compounds Required to Make Gels The unreacted powder (produced by lyophilisation of the manufacturing mixture after incubation at different time, step c)) was re-suspended in Tris-Buffer (Tris 50 mM, pH 7.6) containing 50 mM calcium chloride to form gels with 2.5% w/v Structural compound dry-mass, and final concentrations of factor XIII and thrombin of 10 U/mL and 0.1 U/mL, respectively (similar to gels produced with prior art method as outlined for FIG. 5. Typical re-suspension volumes range from 50 to 1000 uL. Physicochemical characteristics of these gels were measured as indicated below and benchmarked with gels produced using the prior art method as shown below.

Gels according to the prior art were produced and tested as outlined for FIG. 5. The tests included concentrations of fully activated FXIII (FXIIIa following the prior art method) of 10 U/mL (as the 100% activation benchmark) and 5 U/mL (as the 50% activation benchmark). To make FIG. 6a, these data were then plotted with values of FIG. 1A depicting gelation time as a function of the manufacturing time (produced as indicated for FIG. 1). Based on the gelation time (FIG. 6A), it seems that FXIII in the manufacturing mixture has an activity after approx. 1 h and 4 h manufacturing time comparable to the 50% and 100% activation benchmark, respectively.

G' of the same samples were plotted in FIG. 6B, and G' similar to the prior art gels (100% activation benchmark) were obtained already after ca. 2 h manufacturing time. This indicates that FXIII in the manufacturing mixture before lyophilisation has not to be fully activated (i.e. compared to the 100% activation benchmark), as FXIII activation may continue and/or be completed during the gelation process, when the lyophilised powder is resuspended with an appropriate buffer (50 mM Tris-buffer, 50 mM CaCl2, pH 7.6). However, activation of FXIII in the manufacturing mixture close to 100% is preferred.

PREFERRED EMBODIMENT

TABLE 1

| | Concentration/activity | supplier |
| --- | --- | --- |
| Human Thrombin | 0.1 U/ml | Sigma |
| Factor XIII | 10 U/ml | Behring |
| Structural compound A | 8-arm poly(ethylene glycol) functionalized with Glutamine-containing substrate (NQEQVSPLERCG-NH2); 2.5% w/v | |
| Structural compound B | 8-arm poly(ethylene glycol) functionalized with Lysine-containing substrate (Ac-FKGGGPQGIWGQERCG-NH2); 2.5% w/v | |
| pH | 7.6 | |
| Buffer | 50 mM Tris-Buffer, pH 7.6 | |
| $Ca^{2+}$ added | 50 mM | |
| Production time | 4 h | |
| Gelation time | ca. 3 minutes | |
| Shear modulus G' | 700-900 Pa | |
| Swelling Q | 37-41 | |

The invention claimed is:

1. A hydrogel precursor formulation in the form of an unreacted powder comprising:
    an activating enzyme, wherein said activating enzyme is thrombin,
    a cross-linking enzyme, wherein the cross-linking enzyme is transglutaminase, wherein the cross-linking enzyme is activatable by the activating enzyme in water with or without a buffer,
    at least one structural compound A, wherein said structural compound comprises at least two distinct compatible reactive groups that bind through a chemical reaction that is catalyzed by the cross-linking enzyme when activated, and accordingly is cross-linkable by a selective reaction mediated by the cross-linking enzyme to form a hydrogel or alternatively a structural compound A and a structural compound B, wherein said structural compound A and said structural compound B comprise compatible reactive groups that bind through a chemical reaction that is catalyzed by the cross-linking enzyme when activated, and accordingly are cross-linkable by a selective reaction mediated by the cross-linking enzyme to form a hydrogel.

2. The hydrogel precursor formulation according to claim 1, wherein the precursor formulation is substantially deprived of divalent ions.

3. The hydrogel precursor formulation according to claim 1, wherein the at least one structural compound comprises an acyl moiety and an amine moiety.

4. The hydrogel precursor formulation according to claim 1, wherein the hydrogel precursor formulation comprises at least one further cross-linkable bioactive compound.

5. The hydrogel precursor formulation according to claim 1, wherein the at least one structural compound is a multi-branched polyethylene glycol.

6. A kit comprising at least one container filled with a hydrogel precursor formulation as claimed in claim 1, and a container with a reaction buffer.

7. The kit according to claim 6, wherein the kit further includes user instructions.

8. The kit according to claim 6, wherein the reaction buffer contains calcium ions in a range from 1 to 200 mM.

9. The kit according to claim 6, wherein the reaction buffer has a pH of 5 to 8.

10. A method of producing a hydrogel comprising:
a) suspending a hydrogel precursor formulation according to claim 1 in a reaction buffer to form a hydrogel precursor solution.

11. The method according to claim 10, further comprising adding a cell suspension to the resuspended hydrogel precursor solution.

12. The method according to claim 10, wherein at least one gel is casted with the hydrogel precursor solution.

13. The method according to claim 10, wherein a gelation time of the hydrogel precursor solution is in a range of 1 to 20 min, and at a temperature in a range of 39.3 to 98.6° F. (4 to 37° C.).

14. A process for the production of a hydrogel precursor formulation in the form of an unreacted powder, comprising:
a) mixing:
an activating enzyme, wherein said activating enzyme is thrombin,
a cross-linking enzyme, wherein said cross-linking enzyme is transglutaminase, wherein the cross-linking enzyme is activatable by the activating enzyme in water, and
at least one structural compound A,
in water either with or without a buffer; and
b) before or after step a), incubating the cross-linking enzyme and the activating enzyme for a sufficient time so that the gel characteristics remain substantially constant independent from a duration of the manufacturing time;
wherein the structural compound comprises at least two distinct reactive groups that bind through a chemical reaction that is catalyzed by the cross-linking enzyme when activated, and accordingly is cross-linkable by a selective reaction mediated by the cross-linking enzyme; and
the components are mixed in step a) under conditions which hinder the cross-linking reaction mediated by the cross-linking enzyme, or alternatively a structural compound A and a structural compound B, wherein said structural compound A and said structural compound B comprises compatible reactive groups that bind through a chemical reaction that is catalyzed by the cross-linking enzyme when activated, and accordingly are cross-linkable by a selective reaction mediated by the cross-linkable enzyme to form a hydrogel.

15. The process according to claim 14, further comprising after a last of steps a) and b) lyophilisation of the mixture.

16. The process according to claim 14, wherein incubation of the mixture obtained in step a) is performed for at least 0.5 hours and at a temperature in a range of 39.3 to 98.6° F. (4 to 37° C.).

17. The process according to claim 14, wherein the cross-linking enzyme has a degree of activation of 50 to 100%, after step b).

18. The process according to claim 14, wherein at least one further cross-linkable bioactive compound is added in step a).

* * * * *